United States Patent
Vilims (10) Patent No.: US 7,660,634 B2
(45) Date of Patent: Feb. 9, 2010

(54) COMBINATION ELECTRICAL STIMULATING AND INFUSION MEDICAL DEVICE

(76) Inventor: Bradley D. Vilims, 3943 Mountainside Trail, Evergreen, CO (US) 80439

( * ) Notice: Subject to any disclaimer, the term of this patent is extended or adjusted under 35 U.S.C. 154(b) by 224 days.

(21) Appl. No.: 11/625,186

(22) Filed: Jan. 19, 2007

(65) Prior Publication Data

US 2007/0179536 A1    Aug. 2, 2007

Related U.S. Application Data

(62) Division of application No. 11/033,591, filed on Jan. 11, 2005, now Pat. No. 7,386,350.

(51) Int. Cl.
A61N 1/18 (2006.01)
A61N 1/30 (2006.01)

(52) U.S. Cl. .......................... 607/117; 607/3
(58) Field of Classification Search .................. 607/117, 607/120, 125
See application file for complete search history.

(56) References Cited

U.S. PATENT DOCUMENTS

| | | | |
|---|---|---|---|
| 5,255,691 A | 10/1993 | Otten | |
| 5,423,877 A | 6/1995 | Mackey | |
| 6,002,964 A | 12/1999 | Feler et al. | |
| 6,053,916 A | 4/2000 | Moore | |
| 6,104,957 A | 8/2000 | Alo et al. | |
| 6,161,047 A | 12/2000 | King et al. | |
| 6,263,225 B1 * | 7/2001 | Howard, III | 600/378 |
| 6,662,055 B1 | 12/2003 | Prutchi | |
| 6,832,115 B2 | 12/2004 | Borkan | |
| 6,845,267 B2 | 1/2005 | Harrison | |
| 6,921,403 B2 | 7/2005 | Cragg et al. | |
| 6,936,024 B1 | 8/2005 | Houser | |
| 7,014,633 B2 | 3/2006 | Cragg | |
| 7,069,087 B2 * | 6/2006 | Sharkey et al. | 607/76 |
| 7,449,019 B2 * | 11/2008 | Uchida et al. | 606/27 |
| 2002/0156512 A1 * | 10/2002 | Borkan | 607/117 |
| 2003/0028147 A1 * | 2/2003 | Aves et al. | 604/164.06 |
| 2003/0181964 A1 * | 9/2003 | Sharkey et al. | 607/96 |
| 2003/0195518 A1 | 10/2003 | Cragg | |
| 2003/0225331 A1 | 12/2003 | Diederich et al. | |
| 2004/0015202 A1 | 1/2004 | Chandler, III et al. | |
| 2004/0039425 A1 | 2/2004 | Greenwood-VanMeerveld | |
| 2004/0064023 A1 * | 4/2004 | Ryan et al. | 600/374 |
| 2004/0082978 A1 * | 4/2004 | Harrison et al. | 607/48 |
| 2004/0127965 A1 | 7/2004 | Borkan | |

(Continued)

OTHER PUBLICATIONS

U.S. Appl. No. 11/678,516, Vilims.

(Continued)

Primary Examiner—Carl H Layno
Assistant Examiner—Yun Haeng Lee
(74) Attorney, Agent, or Firm—Sheridan Ross PC (57) ABSTRACT

A combined electrical and chemical stimulation lead is especially adapted for providing treatment to intervertebral discs. The combination lead may be placed proximate to intervertebral disc cellular matrix and nucleus pulposus tissue to promote tissue regeneration and repair, as well as nociceptor and neural tissue modulation. The stimulation lead includes electrodes that may be selectively positioned along various portions of the stimulation lead in order to precisely direct electrical energy to stimulate the target tissue. The lead also includes a central infusion passageway or lumen that communicates with various infusion ports spaced at selected locations along the lead to thereby direct the infusion of nutrients/chemicals to the target tissue.

13 Claims, 4 Drawing Sheets

U.S. PATENT DOCUMENTS

| | | | |
|---|---|---|---|
| 2004/0230273 | A1 | 11/2004 | Cates et al. |
| 2004/0243206 | A1 | 12/2004 | Tadlock |
| 2005/0277918 | A1 | 12/2005 | Shah et al. |
| 2006/0155342 | A1 | 7/2006 | Vilims |
| 2006/0155343 | A1 | 7/2006 | Vilims |
| 2006/0217705 | A1 | 9/2006 | Godara et al. |
| 2008/0009927 | A1 | 1/2008 | Vilims |

OTHER PUBLICATIONS

An et al.; "Biological Repair of Intervertebral Disc"; Spine, 2003, vol. 28, No. 15S; pp. S86-S92.

An et al.; "Intradiscal Administration of Osteogenic Protein-1 Increases . . . " SPINE, vol. 30, No. 1, pp. 25-32.

Ben-Yishay; News & Highlights—IDET—a new procedure for discogenic back pain; http://www.neurospinewi.com/newsletters/IDET.html; printed Dec. 22, 2004; 3 pages.

De Mattei et al.; "Effects of Pulsed Electromagnetic Fields on Human Articular Chondrocyte Proliferation"; Connect Tissue Res., 2001, vol. 42, No. 4, pp. 269-279.

Ganey et al.; "Disc Chondrocyte Transplantation in a Canine Model: A Treatment for Degenerated or Damaged Intervertebral Disc"; SPINE, 2003, vol. 28, No. 23; pp. 2609-2620.

Gruber et al., "Biologic Strategies for the Therapy of Intervertebral Disc Degeneration"; Expert Opinion on Biological Therapy, 2003, vol. 3, No. 8, pp. 1209-1214.

IDET Procedure; http://www.thepainrelief.com/idet_idet.shtml; printed Dec. 22, 2004; 2 pages.

Intradiscal Electrothermal Therapy; http://www.emedicine.com/neuro/topic707.htm; printed Dec. 22, 2004; 8 pages.

Mathews et al.; "Treatment of mechanical and chemical lumbar discopathy by dextrose 25%"; J Minim Invasive Spinal Tech, vol. 1, Inaugural 2001; pp. 58-61.

O'Neill et al.; "Percutaneous Plasma Decompression Alters Cytokine Expression in Injured Porcine Intervertebral Disc"; Spine J., 2004, vol. 4, No. 1, pp. 88-98.

SpineCath Intradiscal Electrothermal Therapy; http://www.spineuniverse.com/displayarticle.php/article217.html; printed Dec. 22, 2004; 3 pages.

Walsh et al.; "In Vivo Growth Factor Treatment of Degenerated Intervertebral Discs"; SPINE, vol. 29, No. 2, pp. 156-163.

Wang et al.; "Up-regulation of Chondrocyte Matrix Genes and Products by Electric Fields"; Clinical Ortho. & Related Research; Oct. 2004, 427S: S163-S173.

Yoon et al.; "The Effect of Bone Morphogenetic Protein-2 on Rat Intervertebral Disc Cells in Vitro"; SPINE, vol. 28, No. 16, pp. 1773-1780.

"Pain Management SInergy System"; Baylis Medical Company Inc., 2006, 2 pages.

International Search Report for International (PCT) Patent Application No. PCT/US06/00312, mailed Jul. 19, 2006.

Written Opinion for International (PCT) Patent Application No. PCT/US06/00312, mailed Jul. 19, 2006.

U.S. Appl. No. 12/033,232, Vilims.

Supplementary European Search Report for European Patent Application No. 06717501, mailed Mar. 31, 2008.

Partial European Search Report for European Patent Application No. 08101856.6, mailed Jul. 3, 2008.

Partial European Search Report for European Patent Application No. 08151981, mailed Jul. 16, 2008.

International Preliminary Report on Patentability for International (PCT) Patent Application No. PCT/US06/00312, issued Jul. 17, 2007.

Supplementary European Search Report for European Patent Application No. 06717501, mailed Aug. 20, 2008.

Partial European Search Report for European Patent Application No. 08101856.6, mailed Oct. 28, 2008.

Extended European Search Report for European Patent Application No. 08151981.1, dated Dec. 9, 2008.

Freeman, et al., "Does intradiscal electrothermal therapy denervate and repair experimentally induced posterolateral annular tears in an animal model?", Spine, Dec. 1, 2003, vol. 28, No. 23, pp. 2602-2608.

* cited by examiner

COMBINATION ELECTRICAL STIMULATING AND INFUSION MEDICAL DEVICE

CROSS REFERENCE TO RELATED APPLICATION

The present application is a divisional of U.S. patent application Ser. No. 11/033,591, filed Jan. 11, 2005, now U.S. Pat. No. 7,386,350, entitled "COMBINATION ELECTRICAL STIMULATING AND INFUSION MEDICAL DEVICE", which is incorporated herein by this reference.

TECHNICAL FIELD OF THE INVENTION

The present invention relates generally to electrical stimulation leads and chemical infusion catheters for treatment of medical conditions, and more particularly, to a system, method and device for providing combined electrical stimulation and chemical/drug infusion for treatment of intervertebral disc ailments.

BACKGROUND OF THE INVENTION

It is known that immersing certain cell types within an electrical field will cause these cells to proliferate thus facilitating tissue repair. One known use of an electrical field for such repair is "in bone" stimulators that are implanted in fractures and/or spinal fusions. Another type of treatment has recently developed for spinal conditions wherein target tissue is stimulated by an electrical lead using radio-frequency energy to induce a thermal lesion in the target tissue. In this type of procedure, the therapeutic benefit is intended to derive from heating the target tissue and not from immersing the tissue in an electric field. Thus, the electrical lead in this treatment is strictly for use in heating the tissue, and there is no therapeutic electrical field generated. Chemical treatment of target tissues has also been developed by use of various types of infusion catheters.

For both electrical and thermal stimulation, an electrical current generator, commonly referred to as a pulse generator, may be used to transmit a pulse of electrical current to an implanted stimulation lead that has been precisely placed to transmit the electrical or thermal energy from the electrodes to the target tissue in order to treat the particular condition. For chemical stimulation, one or more drugs or nutrients are delivered by a pump that transfers a desired quantity and frequency of the drug/nutrient through an infusion port of the catheter to the target tissue. For chemical stimulation as well as electrical/thermal stimulation, implanted pumps and generators can be used to deliver the electrical and chemical stimulation as opposed to transdermal delivery devices. More particularly, implanted pulse generators (IPG) as well as implanted drug dispensers (IDP) are commonly used so that patients do not have to return to a medical facility each time treatment is to be conducted.

One relatively new procedure has been developed to treat discogenic back pain. As an alternative to other surgical procedures for patients who suffer from back pain caused by certain types of disc disorders, this new procedure is made possible by use of thermal stimulation leads that provide precise temperature control in the delivery of thermal energy to target tissue. This procedure, commonly referred to as intradiscal electrothermal annuloplasty (IDET) was initially believed to function by cauterizing nerve endings within the disc wall to assist in reduction of pain, and the heat produced by the stimulation leads would also thicken the collagen of the disc wall thereby promoting healing of the damaged disc. Due to age, injury or other conditions, cracks or fissures may develop in the wall of the invertebral disc causing a chronic source of pain in many patients. Additionally, the inner disc tissue (nucleus) will frequently cause the disc to bulge or herniate into the fissures in the outer region of the disc, thus causing nerve tissue therein to generate pain signals. IDET has proven in some cases to be a minimally invasive procedure to treat these types of disc ailments. However, recent research, and clinical experience has cast doubt on the reasons why the procedure results in a healing response of the target tissue. It is now believed that the thermal energy imparted to the disc creates an injury pattern that in some discs results in a repair response. The results of IDET are better characterized as inconsistent and this approach is a very inefficient and marginally effective means of producing a restorative response.

Combination electrical stimulators and chemical infusion catheters are known for purposes of treating various spine and brain ailments. One reference that discloses such a combination device is the invention in U.S. Publication No. US2004/0243206. This reference specifically discloses a combination electrical and stimulation lead for stimulation of a person's nerve tissue in the brain. One or more electrodes are located along the lead body and are adapted to be positioned proximate the target nerve tissue and to deliver electrical stimulation pulses transmitted through the lead to the target nerve tissue. One or more infusion ports located along the lead body are adapted for placement proximate the target nerve tissue and to deliver chemical stimulation pulses transmitted through the lead to the target nerve tissue.

While combination electrical and stimulation leads may be known, special considerations must be made for use of such devices for intervertebral disc treatment.

The intervertebral disc (IVD) provides separation, shock absorption, and controlled motion between vertebral bodies. The disc is comprised of a central nucleus of a semi-fluid mass of mucoid material, (nucleus pulposus), an outer more dense collagen ring (annulus fibrosis), and a thin, metabolically active cellular layer separating the nucleus and the outer collagen ring, referred to as the annular nuclear interface/transitional zone. Disc nutrition is tenuous at best and is provided by diffusion through the vertebral end plate in contact with the outer surface of the disc. As a result, a disc has limited ability to heal or regenerate.

Placement of a stimulation lead within a disc can be quite difficult. Because a disc does not have a uniform density, known stimulation leads can be quite difficult to place and may require the attending physician to make multiple attempts for proper placement or abandon the procedure. Of course, multiple placement attempts greatly increase the invasive nature of the procedure and therefore create unnecessary tissue damage and increased risk. Inability to perform the procedure denies the patient a therapeutic option. Improper placement of the stimulation lead can also result in the undesirable cauterization of nerve tissue that is not contributing to the chronic pain or other ailments. Because of the overall metabolically inactive nature of the disc, it is also important that chemical infusion be precisely targeted to contact the damaged area of the disc with the delivered chemicals/nutrients otherwise inaccurate delivery to non-damaged portions of the disc can reduce the effectiveness of the procedure. Thus, there is a need for a combination electrical and chemical stimulation lead that can be precisely placed with a high rate of success on a first attempt.

The IVD is also a motion segment of the body that is subjected to many flexion/extension/rotation cycles every day. In some procedures, it may be necessary to keep the stimulation lead emplaced for long periods of time, such as weeks or perhaps months. Thus, it is desirable to have a stimulation lead that maintains a small profile, yet is resilient enough to withstand the risk of permanent deformation or shearing during treatment and removal of the stimulation lead after treatment.

SUMMARY OF THE INVENTION

In accordance with the present invention, a combined electrical and chemical stimulation device is provided that is especially adapted for treatment of intervertebral disc ailments. The stimulation device is in the form of a stimulation lead designed to be placed in the disc percutaneously through an introducer needle using an extra-pedicular approach; however, micro-surgical or open-surgical techniques may also be utilized. More specifically, the device of the present invention is specifically designed to facilitate placement proximate to the metabolically active cellular, nuclear, annular interface layer by use of one or more selected embodiments including a straight, curved or bent tip, as well as a variable stiffness tip. Selection of one of these embodiments allows the physician to precisely navigate the lead through the nucleus of the disc. In yet another embodiment of the present invention, the stimulation lead may be placed directly into the nuclear annular interface by use of a introducer needle having a bent tip, and use of a stimulation lead having a straight tip that can take a substantially linear path to reach the target tissue.

The structure of the stimulation lead of the present invention is characterized by an elongate and tubular shaped body including one or more electrodes located along selected portions of the lead body and adapted for positioning proximate the target tissue to deliver electrical stimulation pulses transmitted through the lead. Preferably, the electrodes extend circumferentially around a selected length or portion of the lead since it is difficult to orient a specific lateral side of the lead against target tissue. One or more infusion ports are also located along the lead body and are adapted to be positioned proximate the target tissue to deliver selected chemicals/nutrients.

Once the stimulation lead is correctly positioned, the lead is then connected to a pulse generator for delivery of electrical energy to the electrodes located on the distal portion of the stimulation lead, and is connected to an infusion pump that provides a controlled delivery of chemicals/nutrients through the lead to the target tissue. Preferably, the electrical pulse generator and infusion pump are implanted medical devices. These devices are also preferably refillable and rechargeable.

Particular embodiments of the present invention provide one or more advantages in terms of navigation of the stimulation lead, as well as placement of the infusion ports and electrodes for effectively delivering electrical and chemical treatment. More specifically, the particular shape of the stimulation lead, as well as the particular placement of the electrodes and infusion ports are especially adapted for delivering the electrical stimulation and chemical infusion to target tissue within a disc. A stiffening or support element may be incorporated in the wall of the stimulation lead to ensure the lead does not prematurely shear or otherwise structurally fail during use and removal. The stiffening element is preferably in the form of an elongate support that extends longitudinally within the wall of the stimulation lead and terminating near the distal tip of the lead.

Further advantages and features of the present invention will become apparent from a review of the following detailed description, taken in conjunction with the drawings.

BRIEF DESCRIPTION OF THE DRAWINGS

Reference is now made to the following detailed description taken in conjunction with the accompanying drawings in order for a more thorough understanding of the present invention.

DETAILED DESCRIPTION

Figure 1:
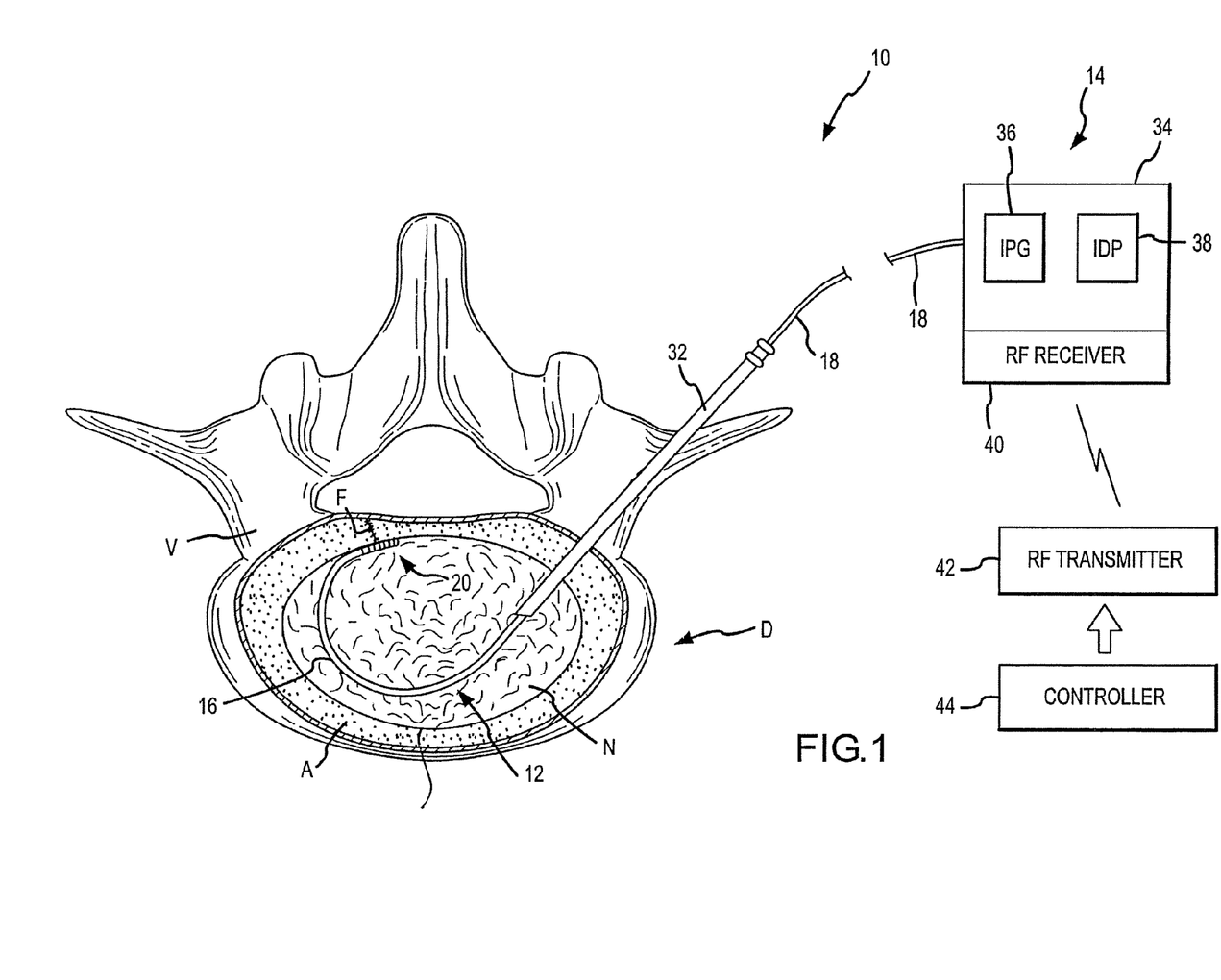
FIG. 1 illustrates the system of the present invention including a stimulation lead inserted in an intervertebral disc, and a stimulation source that provides a controlled delivery of electrical field energy and chemicals/nutrients through the stimulation lead.
Figure 2:
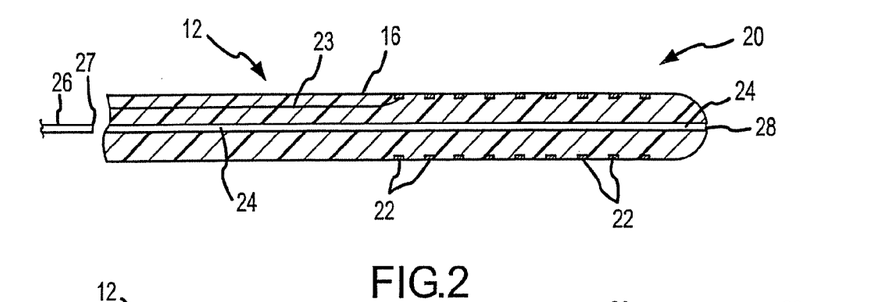
FIG. 2 is a greatly enlarged cross-section of the working distal portion of one preferred embodiment of the stimulation lead of the present invention.

Referring to FIGS. 1 and 2, the system 10 of the present invention is shown that includes a combination electrical and chemical stimulation device 12, a stimulation source 14 that communicates with the stimulation device 12 for delivering electrical energy and chemicals to the stimulation device, and an interventional device such as an introducer needle 32 that allows introduction of the stimulation lead into the disc. The stimulation device 12 is shown as inserted within an intervertebral disc D. The combination device 12 more particularly includes a percutaneous electrical and chemical stimulation lead 16 in the form of an elongate tubular member having a desired length and diameter allowing the lead 16 to be placed within the intervertebral disc of the patient to be treated. The working distal portion 20 of the stimulation lead 16 provides the desired stimulation through a plurality of electrodes 22 which are selectively positioned on the distal portion 20, along with a plurality of infusion ports 30 which allow delivery of chemicals/nutrients to target tissue. The proximal portion of the stimulation device 12 can be referred to as a lead extension 18 that connects to the stimulation source 14. The lead extension 18 can be made of the same type and diameter material as the stimulation lead 16, or may be made of a different type of material and diameter.

Referring specifically to FIG. 2, in a first embodiment of the stimulation lead, a plurality of circumferentially extending electrodes 22 are positioned at the distal portion 20. The electrodes 22 are also spaced longitudinally along the distal portion 20. The electrodes produce an array of electrical field energy, and the target tissue is immersed in the electrical field. One or more electrical conductors 23 extend through the interior of the stimulation lead 16 in order to transmit the electrical impulses to the electrodes 22. It is preferable to utilize a single conductor 23 along the major length of the lead, and then provide branch conductors (not shown) at the distal portion 20 that then extend to contact the various electrodes. The branch conductors could be a linearly arranged set of wire extensions extending between each electrode, or any other advantageous combination of wire conductors to interconnect the electrodes. Use of a single conductor is a more robust design as opposed to multiple smaller conductors that are more prone to breakage as a result of the motion cycles of the ISD. It is also contemplated that the electrodes could be a single electrode wound in a helical pattern about the distal portion 20. Thus in this helical pattern, only one conductor 23 would be required with no additional branch conductors. In order to generate the desired intensity and size electrical field, the electrodes 22 can be disposed on the distal portion in a pattern or arrangement that best suits the electrical field to be generated. For example, in the helical pattern, the electrode could be wound with a tighter pattern to generate a more intense field, while a looser more spaced pattern would generate a less intense field. Of course, the particular signal or impulse current provided to the electrodes also determines the intensity of the field generated.

In order to provide chemical infusion, a central lumen or passageway 24 is formed through the stimulation lead. The central lumen 24 may extend completely through the lead thereby forming a distal opening 28 in the stimulation lead and providing one infusion port that is directed distally of the stimulation lead.

The stimulation lead 16 may be made of a homogeneous material, or may be made of differing materials that cause the stimulation lead to have either a more progressively stiff or more progressively flexible characteristic as the lead extends in the distal direction. Depending upon the manner in which the stimulation lead is to be emplaced, it may be desirable to use either the more progressively stiff or more progressively flexible arrangement.

In accordance with the method of the present invention, a stylet (not shown) is first inserted through the introducer needle 32. The introducer needle 32 is emplaced by penetrating the skin and muscle tissue, and ultimately into the disc D. When the introducer needle has penetrated the disc, the stylet is removed and the stimulation lead 16 is then inserted through the lumen of the introducer needle.

Referring again to FIG. 1, the stimulation lead 16 is illustrated as being emplaced within the disc D. This disc D is shown in cross section along with an adjacent vertebra V. The stimulation lead 16 is shown as taking an arcuate or curved path through the disc nucleus N in order to be precisely positioned at the area of the disc to be treated, illustrated as a fissure F which has developed adjacent the spinal fluid sac (not shown). The other primary features of the disc D are also illustrated including the annulus fibrosis A and the thin layer L defining the annular nuclear interface/transitional zone.

The stimulation source 14 is preferably an implantable medical device 34 including both an IPG (implantable pulse generator) 36 and an IDP (implantable drug dispenser) 38. The implantable device 34 could be contained within a single structural housing, or two separate housings, one for the IPG 36, and one for the IDP 38. The IPG and IDP can both be self-contained devices with internal control for preset delivery of electrical and chemical pulses. Alternatively, an external controller 44 could be used to modify the desired treatment protocol by use of RF transmission wherein an implantable RF receiver 40 is integrated with the IPG 36 and IDP 38. The RF receiver 40 could also be housed within the same implantable medical device 34, or could be a separate implanted device. An external RF transmitter 42 transmits RF signals to control the delivery of electrical stimulation and chemicals to the stimulation lead 16. A controller 44 provides the specific instruction set for transmission by the RF transmitter 42.

Figure 3:
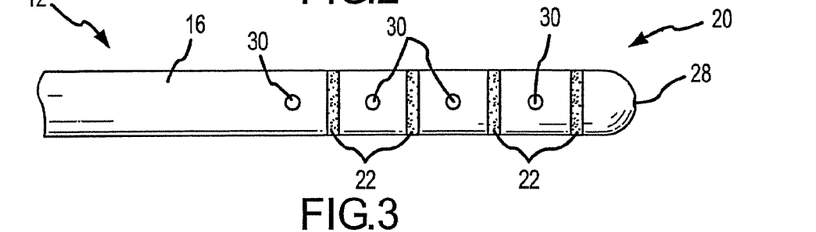
FIGS. 3-7 are greatly enlarged side or elevation views illustrating other preferred embodiments of the stimulation lead.

Referring to FIG. 3, a different arrangement is illustrated with respect to the location of the electrodes 22, and the single infusion port at distal opening 28 is supplemented with a plurality of additional infusion ports 30. In this embodiment, fewer electrodes are incorporated, yet additional infusion ports 30 are provided that are spaced longitudinally along the length of the lead 16 and placed between the electrodes 22.

Figure 4:
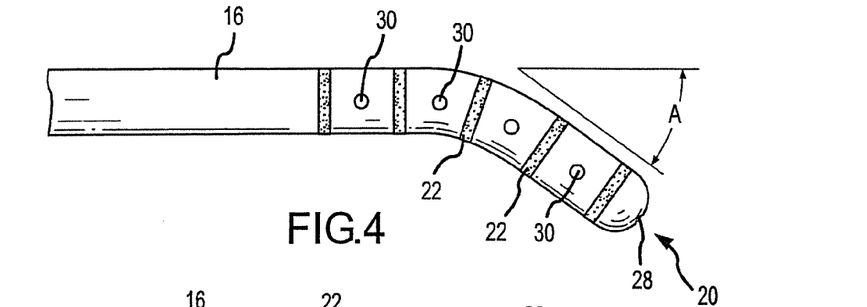

FIG. 4 shows another embodiment with a different arrangement of electrodes 22 and infusion ports 30 as well as a modification of the stimulation lead shape to include a bent distal tip having a chosen bend angle. The bend angle helps define the path of travel of the lead within the disc nucleus during emplacement. In other words, imparting a particular bend angle on the distal tip of the stimulation lead causes the stimulation lead to travel in an arcuate path such as shown in FIG. 1. Imparting a greater bend angle on the lead results in the stimulation lead traveling in a tighter arcuate path, while imparting a lesser bend angle generally results in the stimulation lead traveling in a broader arc or arcuate path.

Figure 5:
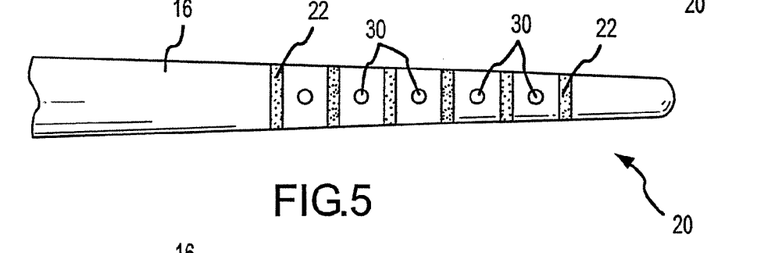

Referring to FIG. 5, another embodiment of the stimulation lead is illustrated wherein the lead has a progressively narrowing diameter towards the distal end thereof. With this type of stimulation lead, travel of the lead through the more dense annulus tissue is facilitated because the distal tip has a smaller frontal profile and is more easily controlled.

Figure 6:
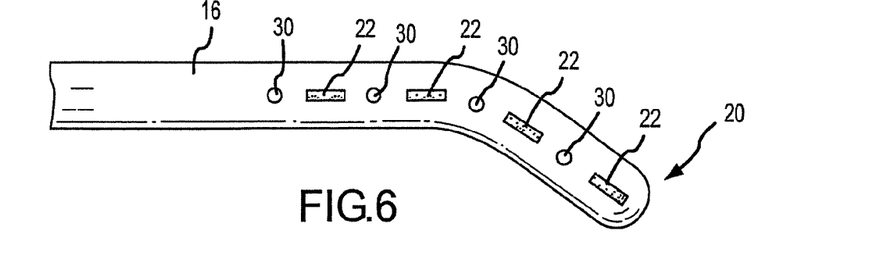

Referring to FIG. 6, yet another embodiment of the stimulation lead is illustrated wherein the electrodes 22 are not formed circumferentially around the distal portion 20, but are formed more linearly along one side of the stimulation lead. Additionally, the infusion ports 30 may have more of an oval shape and be larger in size which facilitates greater volumetric infusion. This embodiment may be preferred when it is desired to more precisely direct the array of electrical energy to the target tissue. The electrical energy array that is created by circumferentially arranged electrodes result in transmission patterns having a radial or circular pattern extending away from the stimulation lead. Thus, a plurality of circumferentially arranged electrodes transmit energy in all directions to tissue that surrounds the stimulation lead. On the contrary, locating the electrodes only along one side or edge of the stimulation lead results in transmission of energy in a more linear and less radial pattern, and directed primarily orthogonal or perpendicular to the axis of the stimulation lead. The embodiment of FIG. 6 also illustrates the distal end as being bent at a desired angle.

Figure 7:
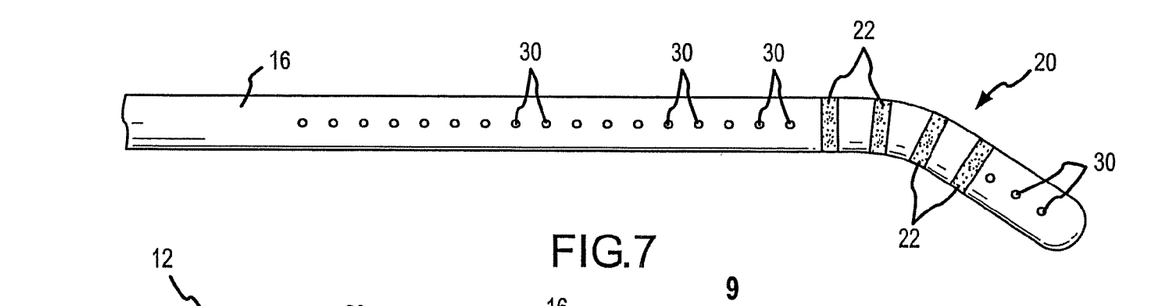

FIG. 7 illustrates yet another embodiment of the stimulation lead wherein the electrodes 22 are concentrated at a particular location, and the infusion ports 30 are spaced in a pattern extending a greater longitudinal length of the lead. A stimulation lead in this particular arrangement may be particularly suitable for repair of a fissure located at a very defined position within the disc, yet if the disc shows great overall degeneration, it is preferable to provide nutrients to a greater length of the annulus whereby the infusion ports 30 can distribute nutrients to a greater length of the annulus.

Figures 8, 9:
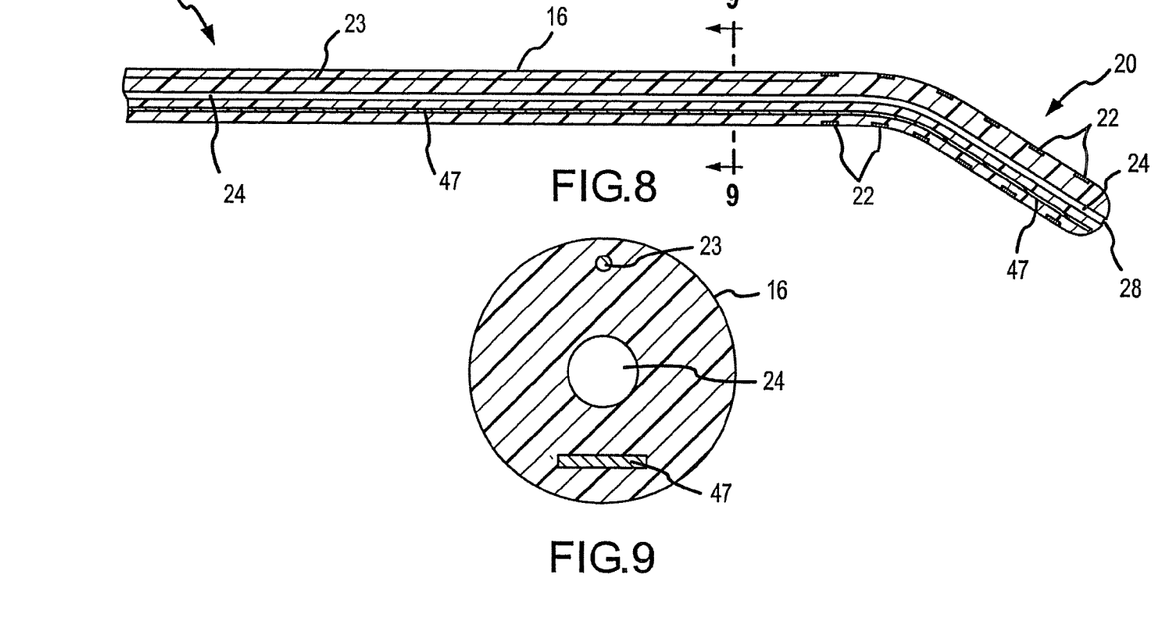
FIG. 8 is a greatly enlarged cross-section of the working distal portion of another preferred embodiment that incorporates a stiffening element.
FIG. 9 is a section taken along line 9-9 of FIG. 8.

FIG. 8 illustrates yet another preferred embodiment of the present invention wherein a stiffening or strengthening member 47 is incorporated within the structural wall of the stimulation lead to provide increased strength to the lead without enlarging the frontal profile of the lead. As shown, the stiffening member 47 is an elongate member that extends longitudinally through the wall of the lead and terminates near the distal end thereof. The stiffening member is malleable to a degree that allows the lead to maintain some desired flexibility during emplacement, but increases the overall shear and torsional strength of the lead to prevent premature failure after emplacement or during removal. The member 47 could be made of a selected metal or thermoplastic approved for medical use.

Figure 10:
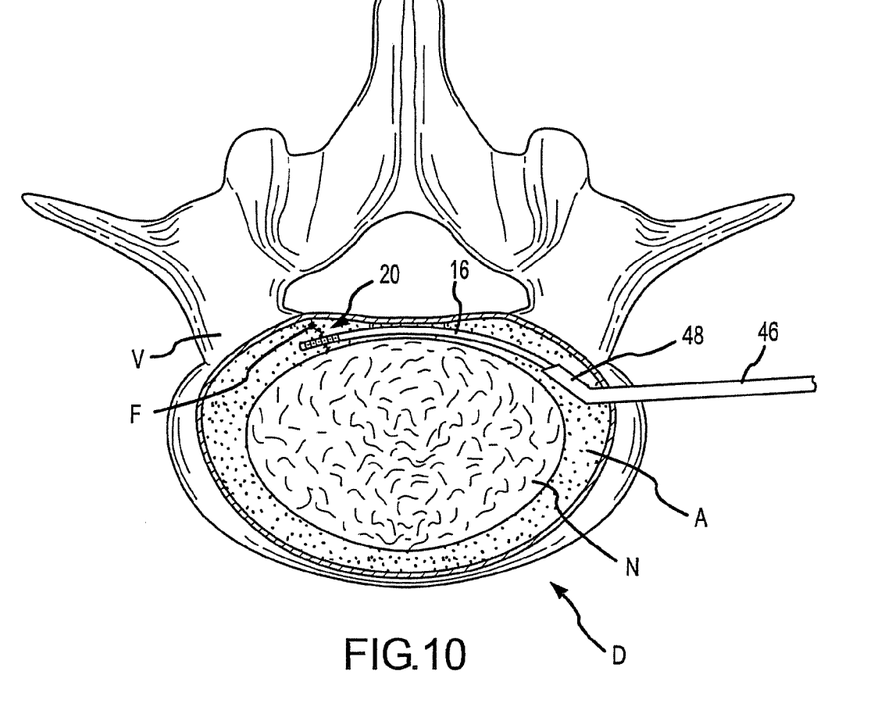
FIG. 10 illustrates another preferred embodiment of the present invention in the form of an introducer needle having a bent distal end for placement of the stimulation lead directly into the nuclear annular interface.

Referring to FIG. 10, yet another embodiment of the invention is shown wherein an introducer needle 46 is not placed within the disc nucleus, but rather is placed only into the disc annulus, and then the stimulation lead 16 extends through the disc annulus to the target tissue, also shown as a fissure F. In this embodiment, it is preferable that the stimulation lead 16 exits the introducer needle through a bent distal portion 48 so that the lead travels in a more parallel fashion within the annulus and along a more linear path to the target tissue. Accordingly, a stimulation lead having a straight tip like shown in FIGS. 2, 3 and 5, would be more suitable according to this embodiment. In the event the distal opening 28 of the lead 16 is of a size which could allow nuclear tissue to clog or block the distal opening 28, a guide wire 26 may be inserted through the lumen 24 of the lead 16, and the distal tip 27 of the guide wire could be placed flush with the distal opening 28 in order to prevent clogging of the distal opening 28, as well as to provide additional rigidity for placement of the stimulation lead 16. If the guide wire 26 is used, then the guide wire 26 is removed prior to connecting the stimulation lead 16 to an IDP and/or IPG. Also, the central lumen may terminate before passing through the distal tip of the lead. Thus, all of the infusion ports 30 would be arranged on the lead to direct chemicals/nutrients in a perpendicular direction away from the axis of the lead.

Figure 11:
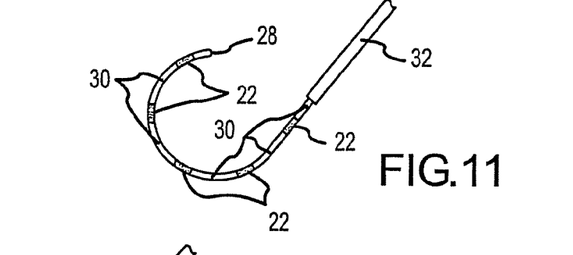
FIGS. 11-13 illustrate further embodiments of the present invention wherein the electrodes and infusion ports are dispersed substantially along the entire length of the stimulation lead.
Figures 12, 13:
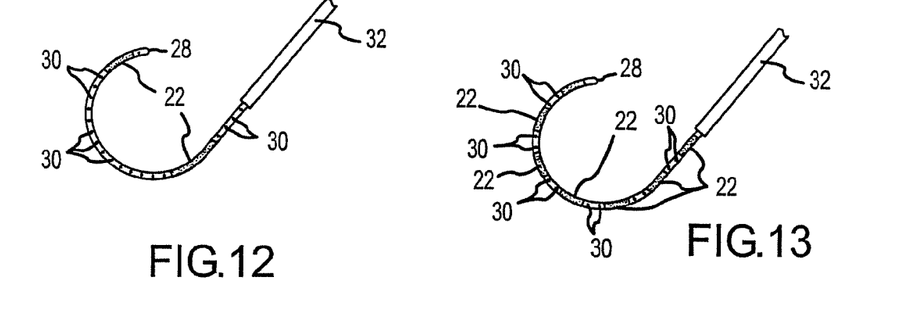

FIGS. 11-13 illustrate yet further embodiments of the present invention wherein the electrodes 22 and infusion ports 30 are dispersed along substantially the entire length of the stimulation lead. In many cases, the disc to be treated has undergone such great degeneration that the entire disc is in need of treatment, as opposed to a more minor degenerative condition such as a single localized fissure. In such cases, it is advantageous to provide both electrical and chemical stimulation to as much of the disc as possible. The embodiments at FIGS. 11-13 show various combinations of the electrodes 22 and ports 30 that provide greater dispersion of the electrical and chemical stimulation. Specifically, the electrodes are larger and are spread out along a greater length of the lead. The infusion ports are also spread out along a greater length of the lead.

Based upon the foregoing, the present invention provides a combination electrical and stimulation lead especially adapted for treatment of disc ailments. The various embodiments provide a treating physician with stimulation leads of various configurations, which optimizes a physician's ability to precisely position the stimulation lead, as well as to precisely direct both electrical and chemical stimulation.

While the above description and drawings disclose and illustrate embodiments of the present invention, it should be understood that the invention is not limited to these embodiments. Those skilled in the art may make other modifications and changes employing the principles of the present invention, particularly considering the foregoing teachings. Therefore, by the appended claims, the applicant intends to cover such modifications and other embodiments.

What is claimed is:

1. A method for treating intervertebral disc ailments, said method comprising:
    inserting an introducer needle into the disc to be treated;
    introducing a combined electrical and chemical stimulation device through said introducer needle and into the disc, said device comprising:
        a stimulation lead having an elongate, tubular configuration, and a central lumen extending therethrough;
        a plurality of infusion ports formed on said stimulation lead and communicating with said central lumen, said infusion ports enabling infusion of chemical/nutrients from the central lumen to tissue located exterior of said stimulation lead;
        a plurality of electrodes positioned on said stimulation lead adjacent said infusion ports, said electrodes communicating with a source of electrical energy for providing electrical/thermal stimulation of tissue adjacent said electrodes, at least one of said infusion ports being located between two adjacent electrodes of said plurality of electrodes, and wherein said stimulation lead has a bend incorporated adjacent a distal end thereof;
    maneuvering the stimulation lead through the disc in an arcuate pattern wherein the distal portion of said stimulation lead is placed adjacent the tissue to be treated;
    inserting an electrical stimulation source into the patient, the electrical stimulation source communicating with said stimulation lead to generate electrical pulses for energizing said electrodes and to deliver electrical/thermal energy to target tissue; and
    inserting a chemical stimulation source into the patient, said chemical stimulation source communicating with said stimulation lead to provide chemical/nutrients through said central lumen and through said infusion ports thereby delivering chemical/nutrients to the target tissue.

2. A method, as claimed in claim 1, wherein:
Said stimulation lead has a straight first portion with at least some of said infusion ports and said electrodes positioned thereon, and a curved shape incorporated at said distal end.

3. A method, as claimed in claim 1, wherein:
said stimulation lead further includes a stiffening member incorporated in said lead for increasing strength of said lead, said stiffening member extending within and substantially along a length of said stimulation lead and not within said central lumen.

4. A method of managing intervertebral disc pain, said method comprising:
    providing a stimulation lead having a plurality of electrodes and a plurality of infusion ports, said electrodes and infusion ports being selectively spaced and arranged with one another;
    implanting the stimulation lead in the disc so that the plurality of electrodes and the plurality of infusion ports lie adjacent to a targeted area within the disc; and
    delivering electrical energy from the electrodes to the disc;
    delivering at least one chemical through the infusion ports into the disc;
    said stimulation lead has a diameter that narrows from a proximal end of said lead toward said distal end thereof, and wherein at least some of said infusion ports and said electrodes are positioned between said proximal end and said distal end.

5. A method, as claimed in claim 4, wherein:
said implanting step further includes the step of imparting a bend angle on a distal end of the stimulation lead in order to assist in implanting the stimulation lead within the targeted area within the disc.

6. A method, as claimed in claim 4, wherein:
said stimulation lead has a straight first portion with at least some of said infusion ports and said electrodes positioned thereon, and a curved shape incorporated at said distal end.

7. A method, as claimed in claim 4, wherein:
said stimulation lead further includes a stiffening member incorporated in said lead for increasing strength of said lead, said stiffening member extending within and substantially along a length of said stimulation lead and not within said central lumen.

8. A method of stimulating a healing response from a damaged intervertebral disc, said method comprising:
providing a stimulation lead having a plurality of electrodes and a plurality of infusion ports, said electrodes and said infusion ports being selectively spaced and arranged with one another;
implanting the stimulation lead in the disc so that the plurality of electrodes and the plurality of infusion ports lie adjacent to a targeted area within the disc;
delivering electrical energy from the electrodes to the disc; and
delivering at least one chemical through the infusion ports into the disc; and
said stimulation lead has a diameter that progressively narrows from a proximal end of said lead toward said distal end thereof, and wherein at least some of said infusion ports and said electrodes are positioned between said proximal end and said distal end.

9. A method, as claimed in claim 8, wherein:
said stimulation lead has a straight first portion with at least some of said infusion ports and said electrodes positioned thereon, and a curved shape incorporated at said distal end.

10. A method for treating intervertebral disc ailments, said method comprising:
inserting an introducer needle into the disc to be treated;
introducing a combined electrical and chemical stimulation device through said introducer needle and into the disc, said device comprising;
a stimulation lead having an elongate, tubular configuration, and a central lumen extending therethrough;
a plurality of infusion ports formed on said stimulation lead and communicating with said central lumen, said infusion ports enabling infusion of chemical/nutrients from the central lumen to tissue located exterior of said stimulation lead;
a plurality of electrodes positioned on said stimulation lead adjacent said infusion ports, said electrodes communicating with a source of electrical energy for providing electrical/thermal stimulation of tissue adjacent said electrodes and wherein said stimulation lead has a bend incorporated adjacent a distal end thereof;
maneuvering the stimulation lead through the disc in an arcuate pattern wherein the distal portion of said stimulation lead is placed adjacent the tissue to be treated;
inserting an electrical stimulation source into the patient, the electrical stimulation source communicating with said stimulation lead to generate electrical pulses for energizing said electrodes and to deliver electrical/thermal energy to target tissue; and
inserting a chemical stimulation source into the patient, said chemical stimulation source communicating with said stimulation lead to provide chemical/nutrients through said central lumen and through said infusion ports thereby delivering chemical/nutrients to the target tissue;
said stimulation lead has a straight first portion with at least some of said infusion ports and said electrodes positioned thereon, and a curved shape incorporated at said distal end; and
said stimulation lead has a diameter that narrows from a proximal end of said lead toward said distal end thereof, and wherein at least some of said infusion ports and said electrodes are positioned between said proximal end and said distal end.

11. A method of stimulating a healing response from a damaged intervertebral disc, said method comprising:
providing a stimulating lead having a plurality of electrodes and a plurality of infusion ports, said electrodes and said infusion ports being selectively spaced and arranged with one another, at least one of said infusion ports being located between two adjacent electrodes of said plurality of electrodes;
implanting the stimulation lead in the disc so that the plurality of electrodes and the plurality of infusion ports lie adjacent to a targeted area within the disc;
delivering electrical energy from the electrodes to the disc; and
delivering at least one chemical through the infusion ports into the disc;
said stimulation lead further includes a stiffening member incorporated in said lead for increasing strength of said lead, said stiffening member extending within and substantially along a length of said stimulation lead and not within said central lumen.

12. A method of stimulating a healing response from a damaged intervertebral disc, said method comprising:
providing a stimulating lead having a plurality of electrodes and a plurality of infusion ports, said electrodes and said infusion ports being selectively spaced and arranged with one another, at least one of said infusion ports being located proximally of at least two adjacent electrodes of said plurality of electrodes, and another one of said infusion ports being located distally of said at least two adjacent electrodes;
implanting the stimulation lead in the disc so that the plurality of electrodes and the plurality of infusion ports lie adjacent to a targeted area within the disc;
delivering electrical energy from the electrodes to the disc; and
delivering at least one chemical through the infusion ports into the disc.

13. A method for treating intervertebral disc ailments, said method comprising:
inserting an introducer needle into the disc to be treated;
introducing a combined electrical and chemical stimulation device through said introducer needle and into the disc, said device comprising:
a stimulation lead having an elongate configuration, and a central lumen extending therethrough;
a plurality of infusion ports formed on said stimulation lead and communicating with said central lumen, said infusion ports enabling infusion of chemicals from the central lumen to tissue located exterior of said stimulation lead;
a plurality of electrodes positioned on said stimulation lead adjacent said infusion ports, said electrodes communicating with a source of electrical energy for providing electrical/thermal stimulation of tissue adjacent said electrodes, at least one of said infusion ports being located between two adjacent electrodes of said plurality of electrodes;

maneuvering the stimulation lead through the wherein the distal portion of said stimulation lead is placed adjacent the tissue to be treated;

inserting an electrical stimulation source into the patient, the electrical stimulation source communicating with said stimulation lead to generate electrical pulses for energizing said electrodes and to deliver electrical/thermal energy to target tissue; and inserting a chemical stimulation source into the patient, said chemical stimulation source communicating with said stimulation lead to provide chemicals through said central lumen and through said infusion ports thereby delivering chemicals to the target tissue.

* * * * *